United States Patent
Kyle et al.

(10) Patent No.: US 9,464,990 B2
(45) Date of Patent: Oct. 11, 2016

(54) CENTIMETER-SCALE HIGH RESOLUTION METROLOGY OF ENTIRE CVD GROWN GRAPHENE SHEETS

(71) Applicant: The Regents of The University of California, Oakland, CA (US)

(72) Inventors: Jennifer Reiber Kyle, Sausalito, CA (US); Cengiz S. Ozkan, San Diego, CA (US); Mihrimah Ozkan, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/412,948

(22) PCT Filed: Jul. 3, 2013

(86) PCT No.: PCT/IB2013/001968
§ 371 (c)(1),
(2) Date: Jan. 5, 2015

(87) PCT Pub. No.: WO2014/033532
PCT Pub. Date: Mar. 6, 2014

(65) Prior Publication Data
US 2015/0192520 A1 Jul. 9, 2015

Related U.S. Application Data

(60) Provisional application No. 61/668,997, filed on Jul. 6, 2012.

(51) Int. Cl.
*G01N 21/64* (2006.01)
*G01N 21/65* (2006.01)

(52) U.S. Cl.
CPC ........ *G01N 21/6458* (2013.01); *G01N 21/643* (2013.01); *G01N 21/65* (2013.01); *G01N 2021/646* (2013.01); *G01N 2021/6417* (2013.01); *G01N 2021/6432* (2013.01); *G01N 2223/406* (2013.01); *G01N 2223/633* (2013.01)

(58) Field of Classification Search
CPC .......... G01N 21/6458; G01N 21/643; G01N 3031/6432
See application file for complete search history.

(56) References Cited

U.S. PATENT DOCUMENTS

2011/0076467 A1* 3/2011 Huang et al. ............. 428/195.1

FOREIGN PATENT DOCUMENTS

WO   WO-2014033532 A2   3/2014
WO   WO-2014033532 A3   3/2014

OTHER PUBLICATIONS

International Application Serial No. PCT/IB2013/001968, International Search Report mailed Apr. 28, 2014, 2 pgs.

(Continued)

*Primary Examiner* — Kiho Kim
(74) *Attorney, Agent, or Firm* — Schwegman Lundberg & Woessner, P.A.

(57) ABSTRACT

A method for quick and easy identification of layer thickness and uniformity of entire large-area graphene samples on arbitrary substrates utilizing fluorescence quenching microscopy in which a polymer mixed with fluorescent dye is applied onto the graphene, then viewing the sample under a fluorescence microscope. A large-scale, high-resolution montage image of the sample is obtained for histogram-based segmentation based on contrast relative to the substrates.

15 Claims, 7 Drawing Sheets

(56) References Cited

OTHER PUBLICATIONS

International Application Serial No. PCT/IB2013/001968, Written Opinion mailed Apr. 28, 2014, 4 pgs.

Kim, Jaemyung, et al., "Visualizing Graphene Based Sheets by Fluorescence Quenching Microscopy", Journal of the American Chemical Society, 132 (2009), 260-267.

Kyle, Jennifer Reiber, et al., "Centimeter-Scale High-Resolution Metrology of Entire CVD-Grown Graphene Sheets", Small, 7 (2011), 2599-2606.

Treossi, Emanuele, et al., "High-Contrast Visualization of Graphene Oxide on Dye-Sensitized Glass, Quartz, and Silicon by Fluorescence Quenching", Journal of the American Chemical Society, 131 (2009), 15576-15577.

International Application Serial No. PCT/IB2013/001968, International Preliminary Report on Patentability mailed Jul. 15, 2015, 6 pgs.

* cited by examiner

CENTIMETER-SCALE HIGH RESOLUTION METROLOGY OF ENTIRE CVD GROWN GRAPHENE SHEETS

CROSS-REFERENCE TO RELATED APPLICATIONS

This application is a U.S. National Stage Filing under 35 U.S.C. 371 from International Application No. PCT/IB2013/001968, filed on Jul. 3, 2013, and published as WO 2014/033532 on Mar. 6, 2014, which claims the benefit of priority under 35 U.S.C. §119(e) to U.S. Provisional Patent Application No. 61/668,997, filed Jul. 6, 2012, which are hereby incorporated by reference herein in their entireties.

STATEMENT OF GOVERNMENT GRANT

The U.S. Government has certain rights in this invention pursuant to Grant Nos.: 080068 awarded by the CMMI Division of the National Science Foundation, 0213695 awarded by the Materials Research Science and Engineering Center on Polymers; 0531171 by the Nanoscale Science and Engineering Center on Hierarchical Manufacturing and the Riverside Public Utilities.

FIELD OF THE INVENTION

The invention relates to characterization of graphene. More particularly, to characterization of large-area graphene films using Fluorescence quenching microscopy.

BACKGROUND OF THE INVENTION

Graphene is a two-dimensional sheet of graphite, consisting of one to ten layers of carbon atoms arranged in hexagonal lattices. Only six years after first fabricating graphene in the laboratory, Geim and Novoselov were awarded the Nobel Prize in physics for their work on graphene.[1] This relatively short time between discovery and recognition is due in part to the fact that graphene was extensively studied theoretically long before it was discovered experimentally. The greatest obstacle to experimental discovery of graphene was the difficulty detecting the graphene sheets. A single-layer graphene is only ~0.4 nm thick[2] and absorbs only 2.3% of incident light.[3] This difficulty was overcome in 2004, when the first graphene sheets were created by mechanical exfoliation of highly ordered graphite and visualized by immobilizing the sheets on oxidized silicon (Si/SiO2) wafers. Light interference in the oxide layer (typically 300 nm thick) changes when it is covered by graphene, allowing identification of the graphene on the substrate through color contrast in the reflected light.[2]

The exceptional electrical, optical, and mechanical properties of graphene make it a promising material for many industrial applications such as solar cells, semiconductor devices, and thermal heat sinks.[4,5] However, the greatest obstacle in its use in industry is high-throughput scaling of the production and characterization of graphene. High-throughput production of graphene can be achieved by growing graphene via chemical vapor deposition (CVD) of carbon atoms on metallic substrates.[6-9] Graphene creation using mechanical exfoliation is labor intensive and only produces a few small graphene samples whereas the size of CVD-grown graphene is only limited by the size of the growth chamber.[10] CVD grown graphene has been developed for many different industrial applications, such as electronic devices, [11-13] solar cells, [14,15] and energy storage.[16] The layer thickness and uniformity of a graphene sample are important parameters that affect the performance and properties of the sample. Additionally, cracks and wrinkles in the graphene sample cause variations in the electronic properties that are unrelated to the quality or thickness of the graphene. These defects are difficult to completely avoid due to complicated growth and processing procedures. Therefore, a high-throughput metrology technique that characterizes an entire CVD grown graphene sample is necessary for industrial applications.

The same obstacle that delayed the discovery of graphene makes high-throughput metrology difficult. Common methods for characterizing graphene thickness are Raman microscopy[17] and atomic force microscopy.[18] While these techniques offer insight into the atomic-scale quality of graphene samples, they are slow and limited to characterizing small regions. To overcome these issues, large-scale optical graphene metrology techniques have been developed that identify the layers of graphene immobilized Si/SiO2 substrates based on their color contrast.[6,19] Although Si/SiO2 substrates offer a simple method for improving the visibility of graphene, they complicate the development of a metrology technique suitably robust for industrial use. This is due to the fact that the color sensitivity of cameras changes between camera models and depends on the illumination intensity. Therefore, the color contrast used to identify graphene layers changes between microscopes and slowly changes on the same microscope as the illumination intensity varies. Additionally, the maximum ideal contrast between graphene layers is limited to ~12%.[20] Therefore, metrology techniques that rely on Si/SiO2 must be calibrated often, a step that requires Raman spectroscopy to identify each individual graphene layer. Finally, many industrial applications, including solar cells and electronic systems on PCB boards, require metrology measurements of graphene samples on substrates other than Si/SiO2.

BRIEF SUMMARY OF THE INVENTION

Here we advance Fluorescence quenching microscopy (FQM) by introducing a method for identifying and counting graphene layers using histogram-based segmentation. Our large-area graphene metrology technique is illustrated in FIG. 1. Briefly, we coat the graphene sample with a dye-polymer solution and image the sample using a fluorescence microscope. To characterize an entire CVD grown graphene sample, we collect a large-scale, high-resolution montage image and process the image to remove the effects of non-uniform illumination. Next, we analyze the histogram of the resulting image to identify the unquenched fluorescence intensity. The intensity ranges within the histogram that correspond to graphene layers are calculated from known contrast ranges relative to the unquenched fluorescence intensity. Finally, the image is segmented by mapping pixels to different graphene layers depending on their intensity values. Utilizing this technique, we achieve high-throughput thickness and uniformity metrology of entire CVD grown graphene samples on a glass substrate. Because the contrast provided by FQM does not depend on the substrate or sensitivity of the microscope, this method does not require additional calibration, allowing for fully-automated metrology measurements. This work introduces a new method for graphene metrology that allows quick and easy identification of CVD grown graphene layers in a large area on arbitrary substrates.

In one embodiment, a method for analyzing graphene is provided comprising performing fluorescence quenching microscopy on a graphene sample, whereby identification of layer thickness and uniformity of the entire area of the graphene sample is achieved on arbitrary substrates.

In another embodiment, the method further comprises providing a solution comprising toluene.

In yet another embodiment, the method further comprises depositing a cured poly(methyl methacrylate) layer over the sample.

In another embodiment, the method further comprises performing montage imaging.

In yet another embodiment, the method further comprises performing a histogram-based segmentation step.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
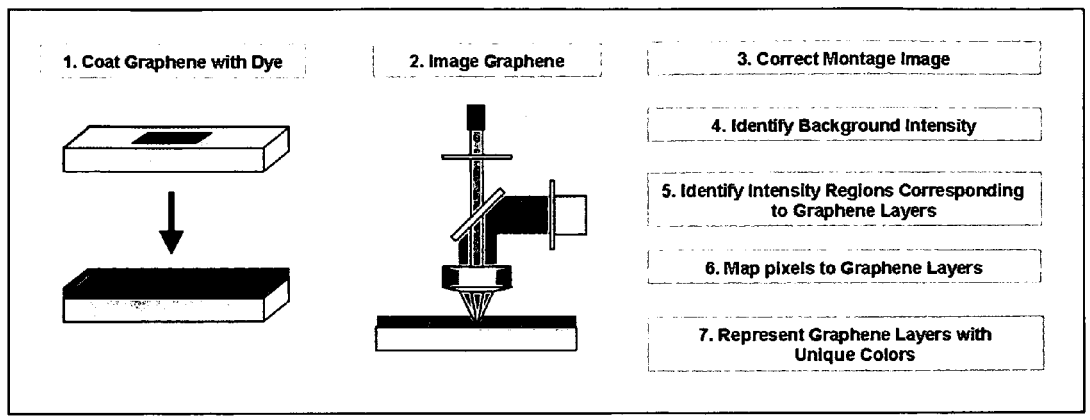
FIG. 1 shows two schematic of large-area, high-contrast graphene metrology technique.
Figure 1:
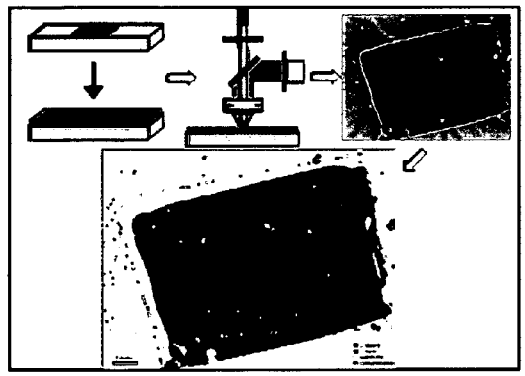

We demonstrate a high-throughput metrology method for measuring the thickness and uniformity of entire large-area chemical-vapor deposition-grown graphene sheets on arbitrary substrates. This method utilizes the quenching of fluorescence by graphene via resonant energy transfer to increase the visibility of graphene on a glass substrate. Fluorescence quenching is visualized by spin-coating a solution of polymer mixed with fluorescent dye onto the graphene then viewing the sample under a fluorescence microscope. A large-area fluorescence montage image of the dyed graphene sample is collected and processed to identify the graphene and indicate the graphene layer thickness throughout the entire graphene sample. Using this metrology method, we study the effect of different transfer techniques on the quality of the graphene sheet. We show that small-area characterization is insufficient to truly evaluate the effect of the transfer technique on the graphene sample. Our results indicate that introducing a drop of acetone or liquid PMMA on top of the transfer PMMA layer before soaking the graphene sample in acetone improves the quality of the graphene sample drastically over immediately soaking the graphene in acetone. This work introduces a new method for graphene quantification that can quickly and easily identify graphene layers in a large area on arbitrary substrates. This metrology technique is well-suited for many industrial applications due to its repeatability and flexibility.

Fluorescence quenching microscopy (FQM) offers an alternative to visualizing graphene using Si/SiO2 substrates and introduces the possibility of high-throughput, large-area metrology of CVD grown graphene samples on arbitrary substrates. FQM is a novel technique for visualizing graphene that is based on the quenching of fluorescence via resonant energy transfer between dye molecules and graphene.[21-23] FQM is an excellent technique for large-scale graphene metrology because it can be performed on arbitrary substrates, imaging time is short, large areas can be measured, and the imaging equipment (a fluorescent microscope) is widely available.[24-27] In FQM, the quenching of dye fluorescence is visualized by spin-coating a solution of polymer mixed with a fluorescent dye onto the graphene sample. While graphene quenches dye fluorescence, the substrate does not. Therefore, graphene regions are identified by dark regions in the fluorescence image of the sample. Currently, FQM has been used to visualize small exfoliated graphene and graphene oxide samples but no attempt has been made to achieve quantitative characterization of the graphene samples such as identifying graphene layers.

Others have identified graphene layers on exfoliated graphene samples using the intrinsic fluorescence of PMMA [1]. This method, however, did not allow for customization of the quenching contrast to achieve maximum contrast between layers. Maximizing contrast between layers is not required for exfoliated graphene samples but is necessary for adequate metrology of CVD graphene samples due to large uniformity variations within the samples. The two major difficulties in identifying graphene layers are developing a sample preparation method that allows repeatable fluorescence quenching between samples and developing a technique to segment the digital image into regions corresponding to different graphene layers.

In one embodiment, in order to measure graphene layers based on contrast, a new polymer solution had to be designed that dissolved both PMMA and DCM and allowed repeatable, uniform coating of the graphene with the fluorescence layer.

Some specific steps that distinguish this method from convention methods:

a. Creating a polymer solution that allows for even and repeatable distribution of the dye layer. This method is the first to use toluene as the solvent for the fluorescent polymer layer. Toluene has a low vapor pressure so the solvent does not evaporate as the liquid polymer is being dispensed in the spin-coating step. Toluene dissolves both PMMA and DCM adequately and we have developed a mixing technique that ensures the dye and polymer are dissolved thoroughly.

b. Montage imaging to image a large area at high resolution. This wasn't done in FQM measurements of exfoliated graphene because exfoliated graphene samples are very small and don't require large-area imaging.

c. Measuring multiple samples and identifying contrast ranges corresponding to graphene layers by analyzing the image histogram. This step is necessary to allow identification of graphene layers based on the measured contrast values.

d. Developing a method for segmenting the image into regions corresponding to different graphene layers by intensity ranges corresponding to the known contrast ranges. This step is necessary to allow graphene layer identification in the digital images.

Results and Discussion

Large-Area High-Contrast Fluorescence Imaging

The contrast between graphene and the substrate can be customized by controlling the thickness of the dye layer, from complete quenching with a dye monolayer[25,28] to negligible quenching with a thick dye layer. In this study, we coated the graphene with a 30 nm-thick dye layer to provide optimal contrast for few layer graphene. After dying the graphene sample, we imaged the graphene with a fluorescence microscope equipped with a mechanical stage. To achieve high-resolution imaging, a 20× (0.75 N.A.) imaging objective was used. With this objective, an image covers a 417×318 µm² area. To image the entire graphene sample, which covers approximately 1 cm², a montage of individual images was collected. This objective can achieve a resolution of 380 nm, however to reduce the noise in the image and keep the size of the montage image file reasonable, we averaged a 4×4 segment of pixels into one final pixel. This resulted in an effective pixel size of 1.24×1.24 µm². The final image is free from noise and does not need to be further filtered.

Figure 2:
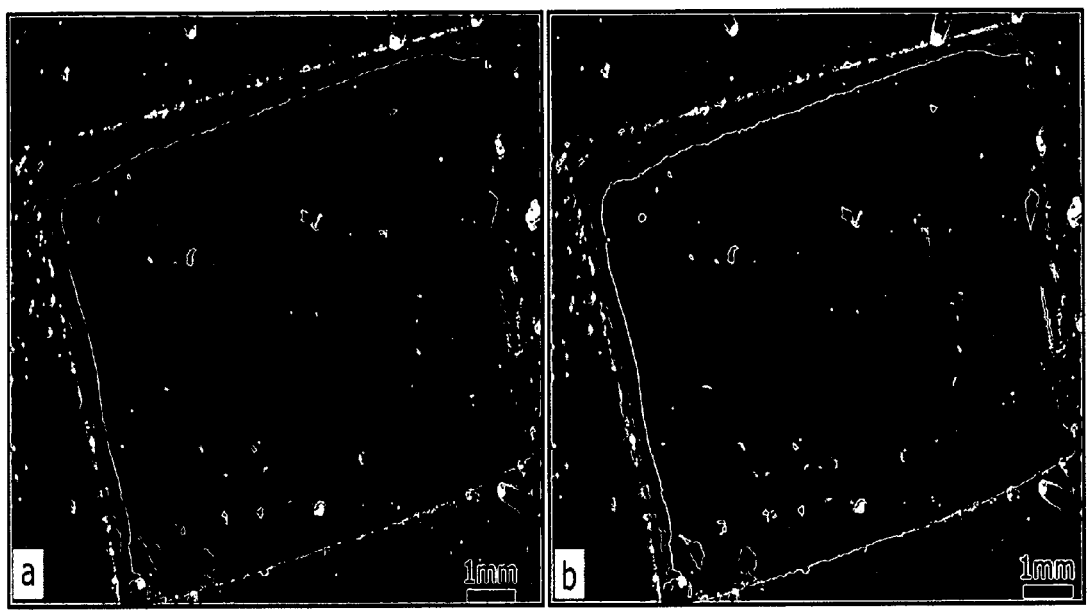
FIG. 2 shows fluorescence image of dyed CVD grown graphene sample (a) before and (b) after background correction.

The fluorescence montage image of single-layer CVD grown graphene is shown in FIG. 2a. The montage consists of 34×46 individual images. Because the illumination across one image is not completely uniform, individual images in the montage image can be identified by their dark outlines. This non-uniform illumination can be corrected using the standard microscopy flatfield correction technique. Briefly, a correction image is created by imaging a uniform fluorescence sample such as a dye layer covering a bare substrate. This image should be created using the same imaging pathway used to create the montage image but only needs to be created once every few months as the illumination source ages. Each area in the montage image that represents an individual image is corrected using $$I_{flat}(x, y) = \frac{I_{original}(x, y)}{I_{correction}(x, y)} \times \overline{I_{correction}}$$ Equation (1)

The flattened image is shown in FIG. 2b. The non-uniform illumination has been entirely corrected. In the flattened FQM image the graphene can be clearly seen and some folds and cracks are apparent.

Identification of Graphene Layers

Identification of the graphene layers is achieved by histogram-based segmentation based on contrast relative to the substrate. The fluorescence intensity If of the dye layer coating the graphene sample is given by $$I_f = (1-f_Q) \ast I_{f0}$$ Equation (2)

where $I_{f0}$ is the original fluorescence intensity of the dye and $f_Q$ is the fluorescence quenching factor which depends on the number of graphene layers and the thickness of the dye layer. Because the glass substrate does not quench the dye fluorescence, the quenching factor is for the substrate is equal to 0 and the fluorescence intensity of the substrate is equal to If0. Contrast between graphene layers and the background is given by the equation $$C = \frac{I_{background} - I_{graphene}}{I_{background}}.$$ Equation (3)

Substituting If0 for Ibackground and $(1-f_Q)$If0 for Igraphene in Equation (3) gives the relationship between the quenching factor and the contrast between the graphene layer and the substrate, $$C = f_Q.$$ Equation (4)

The fluorescence intensity of the graphene layers and the substrate can vary between images due to variations in the illumination intensity. However, the contrast between the graphene layers and the substrate is determined by the quenching factor, which is constant across samples and microscopes and depends only on the dye layer thickness.

The first step in our segmentation algorithm is measuring Ibackground. This is achieved by analyzing the image histogram. Two major peaks are apparent in the histogram of the corrected fluorescence image of the CVD grown graphene sample (FIG. 2c). The peak at higher fluorescence intensities represents the substrate while the peaks at lower intensities represent the graphene. Ibackground is the intensity value that correlates to the apex of the substrate peak in the histogram. To ensure that the peak corresponding to the substrate is easily identifiable in the image histogram, it is important to design the montage image collection so that the substrate covers a significant portion of the fluorescence image. Once Ibackground is determined, the contrast value for each pixel is calculated according to $$C(x, y) = \frac{I_{background} - I(x, y)}{I_{background}}.$$ Equation (5)

Next, the image is segmented according to the pixel contrast value. Our measurements on multiple graphene samples found that for a 30 nm-thick dye layer, the contrast range for single-layer graphene is 0.35-0.58, 0.58-0.75 for two-layer graphene, and 0.75-0.8 for three or more graphene layers. Ideally, the contrast for different layers would be discrete values instead of value ranges. This would be the case for exfoliated graphene samples. CVD grown samples, however, have variations on the nanometer scale which cannot be adequately resolved due to the diffraction resolution limit of light. The signal from these regions is averaged to obtain the intensity value for each pixel in the collected image. Therefore the intensity peaks in the fluorescence image histogram resemble Gaussian peaks and represent the low-passed version of the ideal discrete peaks.

In addition to identifying graphene layers, our segmentation algorithm identifies contamination on the graphene surface. This is possible because the contamination particles obstruct the distribution of dye as it is spun onto the graphene sample, causing the dye to build up around the particles which results in regions where the fluorescence intensity is brighter than the fluorescence of the flat substrate. Similarly, very large contamination blocks the flow of dye, which creates regions with a thinner dye layer. This can lead to incorrect identification of the graphene layers. Therefore, detecting contamination in the segmentation algorithm is important for accurate interpretation of the segmentation results. The contrast range for pixels darker than Ibackground is 0-1 while pixels brighter than Ibackground have negative contrast values. The segmentation algorithm maps pixels to graphene layers, Ln, according to $$L_n(x,y) = \begin{cases} 3 & 0.75 \le C(x,y) < 0.8 \\ 2 & 0.58 \le C(x,y) < 0.75 \\ 1 & 0.35 \le C(x,y) < 0.58 \\ 0 & -0.2 \le C(x,y) < 0.35 \\ -1 & C(x,y) < -0.2, C(x,y) \ge 0.8 \end{cases} \quad \text{Equation (6)}$$

where −1 indicates surface contamination, 0 indicates the substrate, and 3 indicates three or more graphene layers. Applying this segmentation algorithm to the flattened montage fluorescence image in FIG. 2b produces the segmented image shown in FIG. 3. In this image, the graphene layers are portrayed using unique colors. The segmented image shows that the graphene sample is entirely single-layer graphene with some easily identifiable cracks and folds consisting of two-layer graphene. The light blue arrows in FIG. 3 indicate regions where large contamination affected the distribution of the dye layer.

Figure 4:
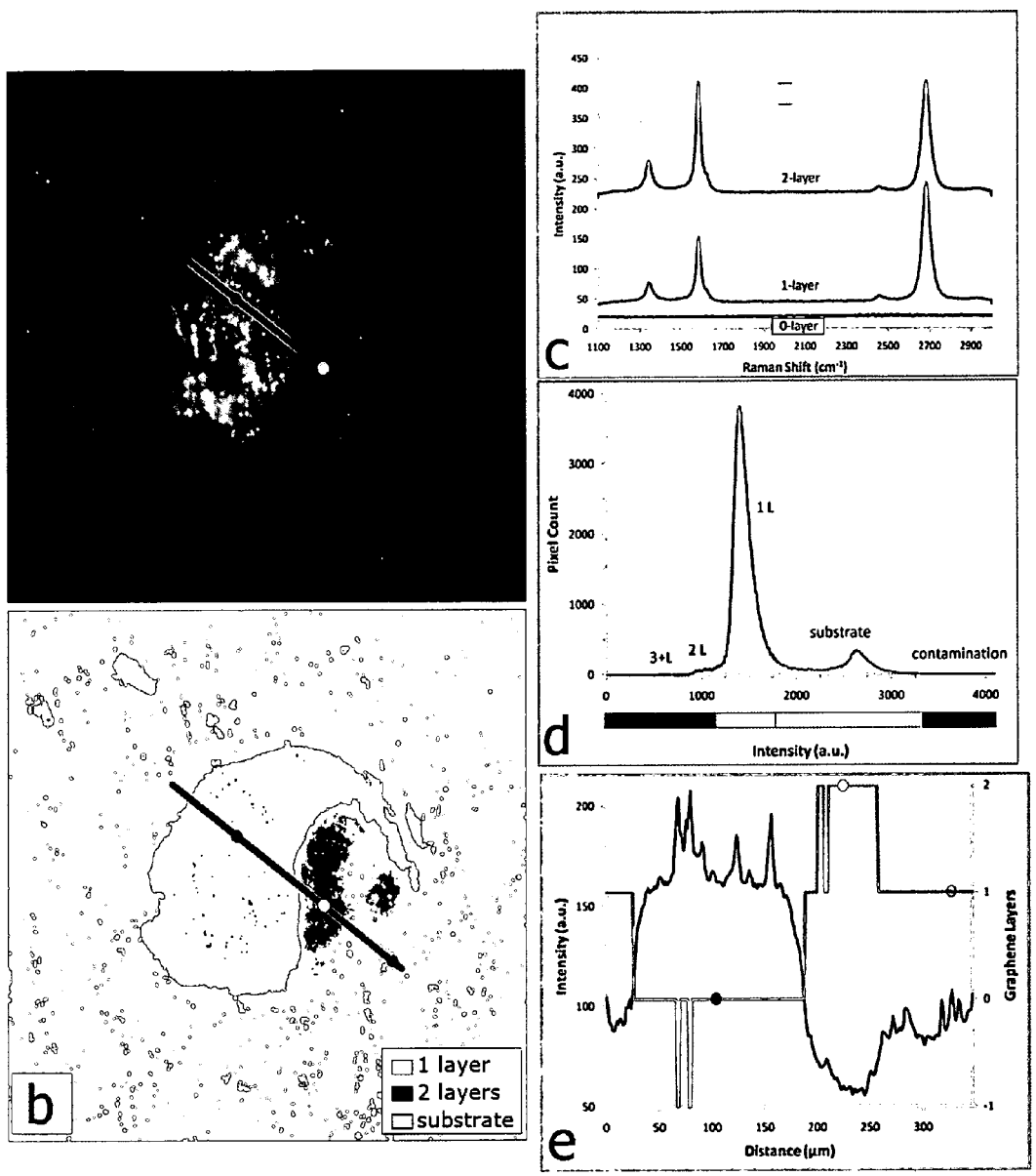
FIG. 4 show (a) FQM and (b) segmented images of CVD grown graphene. (c) Raman spectra recorded at colored dots in (a) and (b). Spectra have been offset for visibility. (d) Histogram of FQM image. Colored regions indicate intensity ranges mapped to different graphene layers in segmentation algorithm. (e) Line profile from (a) and (b) showing FQM signal (red line), layer count from segmented image (blue line), and layer count from Raman measurements (colored dots).

To compare the results of our segmentation algorithm with Raman microscopy measurements, we consider a small region from the large-area fluorescence image where the graphene sample exhibits a large crack and a fold. The fluorescence image of this region is shown in FIG. 4a and the segmented image is shown in FIG. 4b. Raman measurements were taken in the areas corresponding to the colored dots in the fluorescence and segmented images. The resulting spectra (FIG. 4c) indicate that the graphene sample is mostly single-layer graphene (green dot and spectrum) with two-layer graphene at the fold (blue dot and spectrum) and no graphene in the crack (red dot and spectrum).[17, 29-31] In the histogram of the fluorescence image (FIG. 4d) intensity ranges mapped to different graphene layers during the segmentation process are indicated. Profiles taken along the lines in the fluorescence and segmented images are compared to the graphene layer thickness measured by Raman microscopy in FIG. 4e. Raman microscopy measurements, indicated by the colored dots in the line profile, agree with the layer thickness identified by the segmentation algorithm. Therefore, Raman microscopy confirms that our segmentation technique accurately measures graphene layer thickness.

Graphene Layer Quality Comparison

To illustrate the usefulness of this metrology technique for applications such as optimizing graphene growth procedures, we compare the quality of graphene samples prepared using different transfer techniques. An important step in the transfer of graphene is dissolving the cured poly(methyl methacrylate) (PMMA) layer that is used to protect the graphene during the etching and transfer steps. The basic technique is to completely dissolve the PMMA by dipping the entire sample in acetone.[32] Recently it was shown that the quality of the CVD grown graphene sample is improved when a drop of liquid PMMA is added on top of the transfer PMMA and allowed to slowly dissolve the transfer PMMA for 30 minutes before the acetone soak.[33] The authors suggested that dissolving the transfer PMMA with liquid PMMA allowed the graphene to relax on the substrate. We propose that similar results can be obtained by adding a drop of acetone instead of liquid PMMA.

Figure 3:
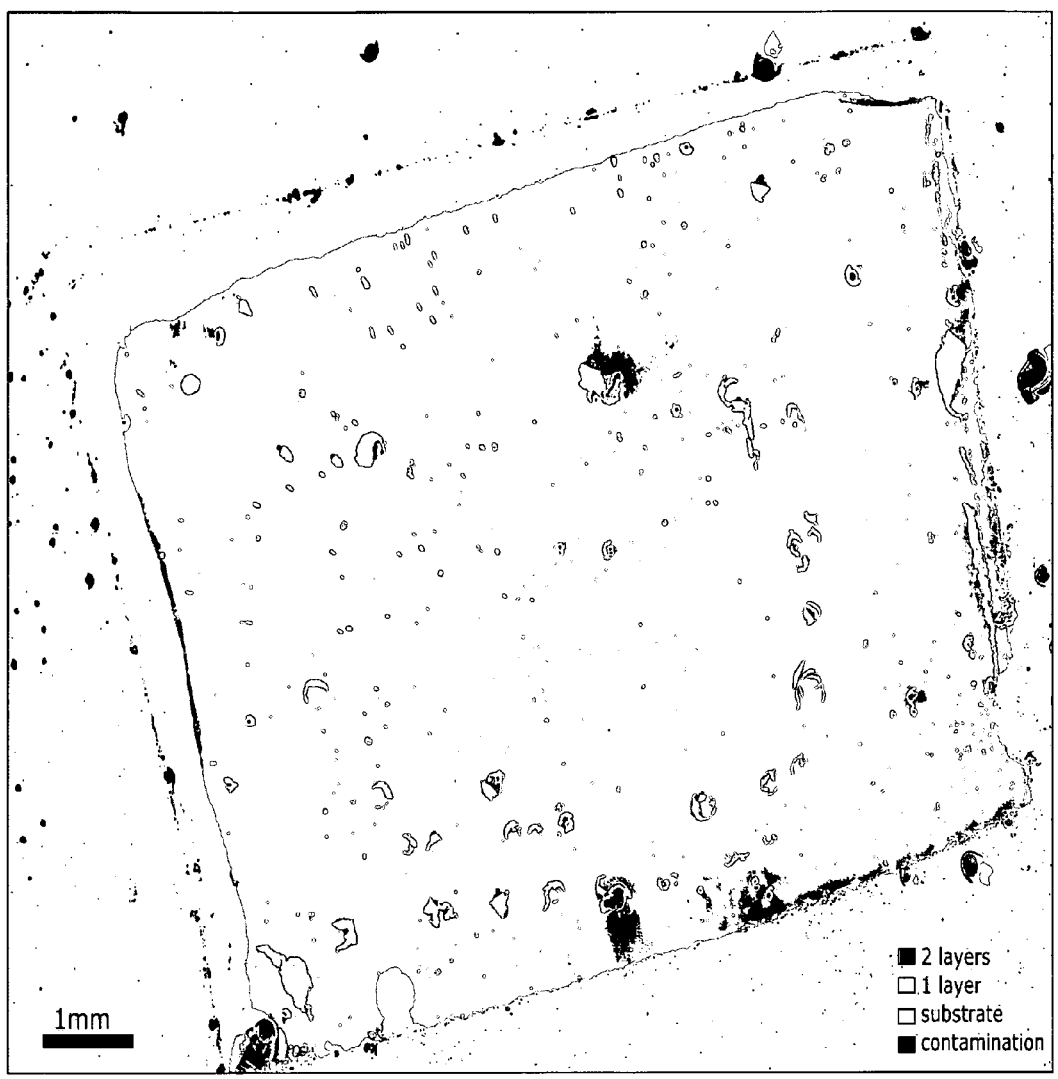
FIG. 3 shows a schematic segmented image of dyed CVD grown graphene sample showing different graphene layers and surface contamination. Arrows show 2 layered areas.
Figure 5:
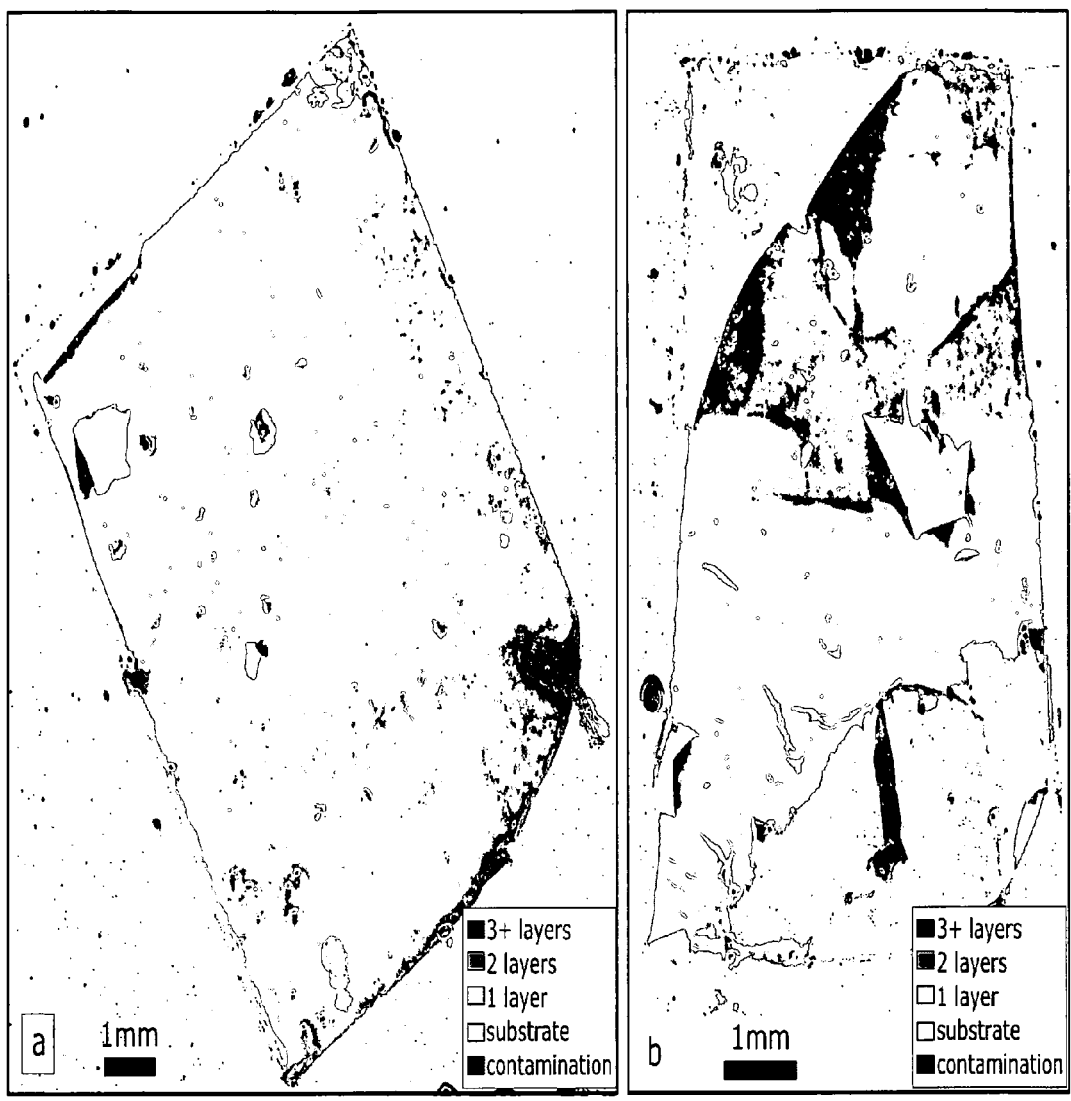
FIG. 5 show segmented image of dyed CVD grown graphene samples prepared using different transfer techniques. (a) Modified technique where a drop of liquid PMMA is added to the transfer PMMA and (b) unmodified technique where the transfer PMMA is directly dissolved by dipping the sample in acetone.

The graphene sample shown in FIG. 3 was prepared by adding one drop of acetone onto the transfer PMMA and allowing it to dry for 30 minutes before soaking the sample in acetone. For the graphene sample shown in FIG. 5a, we added one drop of liquid PMMA onto the transfer PMMA and allowed it to dry for 30 minutes. As a control, the graphene sample in FIG. 5b was prepared by following the unmodified basic transfer technique, where the sample is directly dipped into acetone to dissolve the PMMA. All three CVD grown graphene samples were grown on the same copper foil substrate, underwent the same etching process, and were dried overnight after they were immobilized onto the glass substrate. The segmented images of the graphene samples clearly show that the quality of the graphene sample is improved by both the acetone drop and PMMA drop methods. The presence of numerous folds and large cracks in the sampled prepared using the unmodified method indicates that the graphene did not adequately relax onto the substrate and was torn when the transfer PMMA was dissolved in the acetone bath. The graphene samples prepared using the acetone drop and PMMA drop methods are of similar quality. Both samples still contain some cracks and folds, indicating an opportunity for further improvement of the transfer method.

Figure 6:
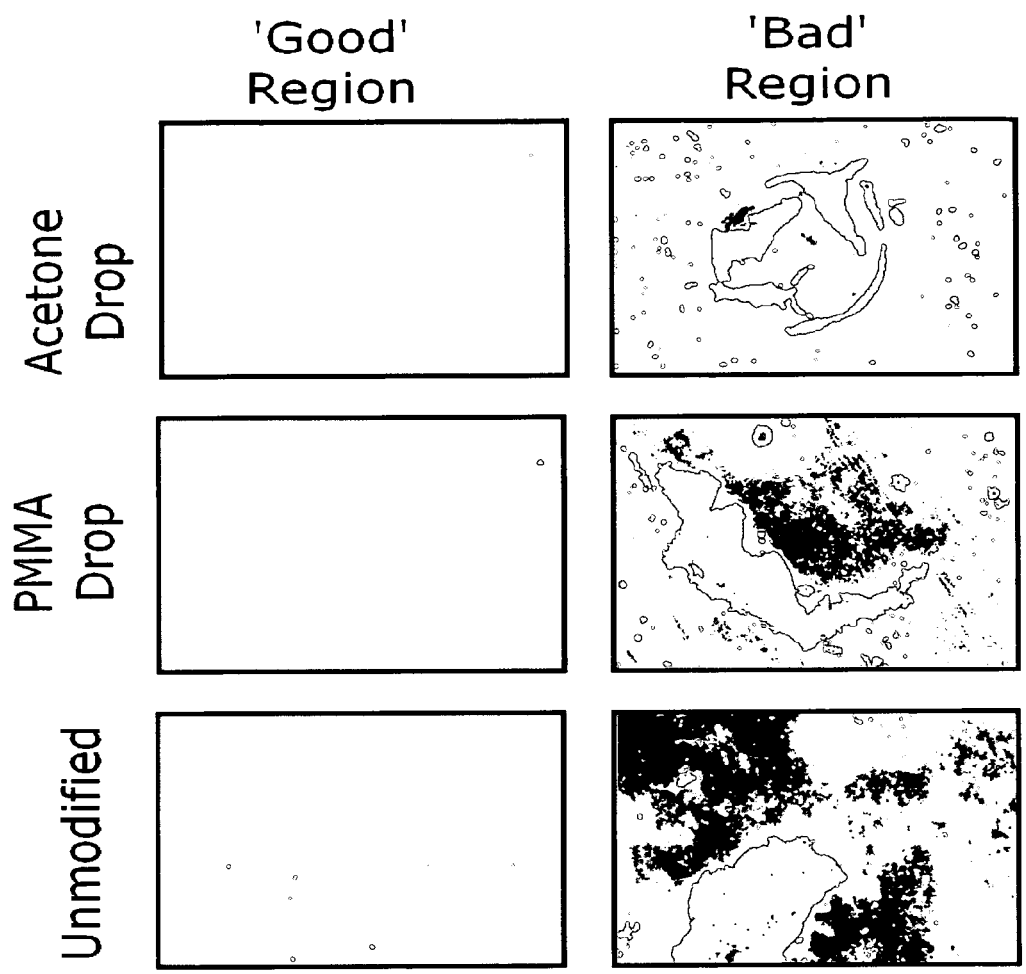
FIG. 6 shows comparison of different regions in the segmented images of graphene samples. Each region covers a 417×318 µm2 area.

FIG. 6 shows 417×318 μm² sections of each graphene sample which represent 'good' and 'bad' regions in the samples. The size of these sections is approximately the size of a single image collected using a 20× objective. Although the large-scale images of the graphene samples show that the modified transfer methods produce graphene samples with improved quality compared to the unmodified transfer method, the small-scale 'good' images indicate that the samples are all of equal quality. It is easy to see how a comparison that only uses small-scale images could be comparing 'good' regions to 'bad' regions in different samples, resulting in incorrect conclusions. Therefore, a large-scale metrology technique is required to accurately compare the quality of CVD grown graphene samples.

CONCLUSIONS

In summary we have introduced a large-scale metrology method for measuring the thickness and uniformity of entire CVD grown graphene samples. This method utilizes FQM to increase the contrast between the graphene layers and the substrate and histogram-based segmentation to identify the graphene layers. Unlike methods based on color contrast created using a Si/SiO2 substrate, this method does not require calibration but is consistent across different samples and microscopes. The contrast ranges for different graphene layers depends on the dye thickness. In this study, we utilized a dye thickness optimized for few-layer graphene. It is easy to see that this method can be extended to thicker graphene samples by increasing the thickness of the dye layer.

Utilizing the large-scale metrology method described in this work, we have evaluated the effect of different transfer methods on the quality of the resulting CVD grown graphene layers. We found that adding a drop of acetone to the sample to dissolve the PMMA layer before dipping the sample in acetone yields graphene samples that are of similar quality to samples where a drop of liquid PMMA was added. Both methods improved the quality of the graphene compared to the basic transfer technique, in which the sample is immediately soaked in acetone. Comparing small-scale images of the different graphene samples revealed that these images do not adequately describe the samples and can lead to incorrect conclusions about the quality of the CVD grown graphene samples. The large-scale metrology technique described in this work allows for fast and accurate evaluation of the quality of entire CVD grown graphene samples. The repeatability and flexibility of this technique make it promising for many industrial applications.

Experimental Methods

Dye-Doped Polymer Preparation and Measurement

The dye mixture was prepared by adding 0.01 wt % 4-(Dicyanomethylene)-2-methyl-6-(4-dimethylaminostyryl)-4H-pyran (DCM, Sigma Aldrich) to 10 mL 1.0 wt % PMMA (Mw~120,000) dissolved in toluene (>99.5%, Fisher Chemical). The low vapor pressure of toluene allows the formation of extremely uniform dye layers. The solution was stirred and heated overnight to dissolve the polymer, then continuously stirred while stored. Immediately before the solution was spun onto the substrate, it was sonicated for 15 minutes. To ensure that any bright spots seen in the FQM image of graphene were due to contamination on the surface, the dye solution was passed through a 0.22 μm filter before being deposited on the substrate. The dye layer was formed by flooding the substrate with the dye mixture then spinning the substrate at 3000 rpm for 60 seconds with a 2-second ramp. Next, the sample was stored in a vacuum desiccator for one hour to completely evaporate the solvent. This step is necessary to achieve consistent contrast measurements for the graphene layers. As the solvent evaporates, the layer thickness decreases which alters the quenching of the dye layer and the contrast between graphene layers and the substrate. The dye layer thickness was determined by forming scratches in the polymer layer with plastic tweezers and measuring the height difference with a Veeco Dektak 8 surface profilometer. The measured absorption and emission peaks for the dye polymer mixture are 470 nm and 560 nm, respectively (see Supplementary Information).

Graphene Sample Preparation for FQM

Centimeter-scale graphene sheets were grown using a 25 μm-thick copper foil (Alfa Aesar, item No. 13382) as a catalyst.[7] The copper foils were pretreated with acetic acid and deionized (DI) water to ensure the surfaces were completely clean and free from oxidation. Next, the pretreated copper foils were loaded into a quartz-tube furnace chamber and heated to 1000° C. in a 2-Torr Ar/H2 (200:200 sccm) atmosphere and thermally annealed for 30 minutes. For the growth of graphene, methane (100 sccm) was introduced into the chamber under 20 Torr for 20 minutes and the chamber temperature was cooled down to 25° C. at a cooling rate of 20° C./minute. The graphene samples were removed from the growth chamber and covered with PMMA by drop-coating and heated at 120° C. for 10 minutes to dry the PMMA layer. The copper foil was then etched in iron(III) chloride (FeCl3) aqueous solution (0.5M) and rinsed thoroughly with hydrochloric acid (3%) and DI water, respectively.

Glass substrates were prepared by cutting microscope slides into 1 in 2 squares and cleaning by gently rubbing with a clean gloved finger and liquid detergent, followed by sonication for 10 minutes each in DI water, toluene, acetone, and IPA and finally blowing dry with a nitrogen stream. Floating graphene samples were fished onto the substrate and allowed to dry overnight. To remove the transfer PMMA from the graphene, the samples were soaked in heated acetone for 30 minutes, soaked in heated IPA for 10 minutes, and dried under a nitrogen stream. The samples were stored in a vacuum desiccator.

Image Acquisition

Fluorescence images of the dye-coated graphene were collected using a BD Pathway 855 HT Confocal microscope. An arc lamp was used as the light source. The illumination light was filtered through a 470 nm (+/−40 nm) bandpass filter and a dichroic filter (520 nm) and focused on the sample using an Olympus 20× objective with a 0.75 numerical aperture. The emitted light was passed through a 542 nm (+/−27 nm) bandpass filter and detected with a CCD camera. BD AttoVision software, which is provided with the Pathway microscope, was used to control the mechanical stage and collect montage images.

Image Processing

All image processing was performed on a standard laptop using Matlab software.

Supporting Information

Figure 7:
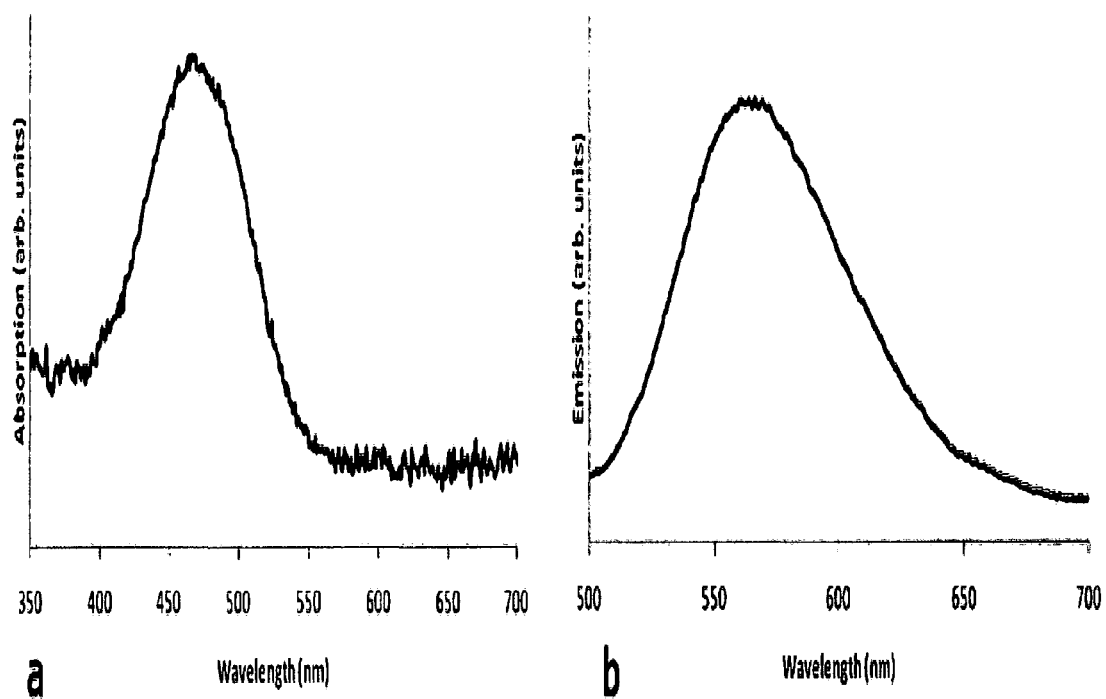
FIG. 7 shows dye-doped polymer absorption and fluorescence emission spectra.

The fluorescence spectrum of dyes depends on the solvent used to dissolve the dye powder. Because the spectra for DCM dissolved in toluene with PMMA have not been previously recorded, we measured the absorption and emission spectra of our polymer dye solution after it was spin-coated onto glass slides. The measured spectra are shown in FIG. 7. The fluorescence collection and emission optics were determined from the peaks in the absorption and emission spectra.

REFERENCES

[1] A. Cho, Science 2010, 330, 159.
[2] K. Novoselov, A. Geim, S. Morozov, D. Jiang, Y. Zhang, S. Dubonos, I. Grigorieva, A. Firsov, Science 2004, 306, 666-669.
[3] R. R. Nair, P. Blake, A. N. Grigorenko, K. S. Novoselov, T. J. Booth, T. Stauber, N. M. R. Peres, A. K. Geim, Science 2008, 320, 1308.
[4] A. Castro Neto, F. Guinea, N. Peres, K. Novoselov, A. Geim, Rev. Mod. Phys. 2009, 81, 109-162.
[5] A. Geim, K. Novoselov, Nat. Mater. 2007, 6, 183-191.
[6] A. Reina, S. Thiele, X. Jia, S. Bhaviripudi, M. Dresselhaus, J. Schaefer, J. Kong, Nano. Res. 2009, 2, 509-516.
[7] X. Li, W. Cai, J. An, S. Kim, J. Nah, D. Yang, R. Piner, A. Velamakanni, I. Jung, E. Tutuc, S. K. Banerjee, L. Colombo, R. S. Ruoff, Science 2009, 324, 1312-1314.
[8] A. N. Obraztsov, Nat. Nanotechnol. 2009, 4, 212-213.
[9] A. Reina, X. Jia, J. Ho, D. Nezich, H. Son, V. Bulovic, M. S. Dresselhaus, J. Kong, Nano Lett. 2009, 9, 30-35.
[10] M. Allen, V. Tung, R. Kaner, Chem. Rev. 2010, 110, 132-145.
[11] Z. Chen, Y. Lin, M. Rooks, P. Avouris, Physica E: Low-dimensional Systems and Nanostructures 2007, 40, 228-232.
[12] J. Lin, D. Teweldebrhan, K. Ashraf, G. Liu, X. Jing, Z. Yan, R. Li, M. Ozkan, R. K. Lake, A. A. Balandin, C. S. Ozkan, Small 2010, 6, 1150-1155.
[13] X. Wang, Y. Ouyang, X. Li, H. Wang, J. Guo, H. Dai, Phys. Rev. Lett. 2008, 100, DOI 10.1103/PhysRevLett. 100.206803.
[14] L. De Arco, Y. Zhang, C. Schlenker, K. Ryu, M. Thompson, C. Zhou, ACS Nano 2010, 4, 2865-2873.
[15] J. Lin, M. Penchev, G. Wang, R. K. Paul, J. Zhong, X. Jing, M. Ozkan, C. S. Ozkan, Small 2010, 6, 2448-2452.
[16] R. Paul, M. Ghazinejad, M. Penchev, J. Lin, M. Ozkan, C. Ozkan, Small 2010, 6, 2309-2313.
[17] A. C. Ferrari, J. C. Meyer, V. Scardaci, C. Casiraghi, M. Lazzeri, F. Mauri, S. Piscanec, D. Jiang, K. S. Novoselov, S. Roth, A. K. Geim, Phys. Rev. Lett. 2006, 97, 187401.
[18] S. Stankovich, D. A. Dikin, G. H. B. Dommett, K. M. Kohlhaas, E. J. Zimney, E. A. Stach, R. D. Piner, S. T. Nguyen, R. S. Ruoff, Nature 2006, 442, 282-286.
[19] C. M. Nolen, G. Denina, D. Teweldebrhan, B. Bhanu, A. A. Balandin, ACS Nano, DOI 10.1021/nn102107b.

[20] P. Blake, E. W. Hill, A. H. Castro Neto, K. S. Novoselov, D. Jiang, R. Yang, T. J. Booth, A. K. Geim, App. Phys. Lett. 2007, 91, 063124.
[21] R. S. Swathi, K. L. Sebastian, J. Chem. Phys. 2008, 129, 054703.
[22] R. Swathi, K. Sebastian, J. Chem. Phys. 2009, 130, DOI 10.1063/1.3077292.
[23] R. Swathi, K. Sebastian, J. Chem. Sci. 2009, 121, 777-787.
[24] J. Kim, L. Cote, F. Kim, J. Huang, J. Am. Chem. Soc. 2010, 132, 260-267.
[25] E. Treossi, M. Melucci, A. Liscio, M. Gazzano, P. Samori, V. Palermo, J. of the Am. Chem. Soc. 2009, 131, 15576-15577.
[26] A. Sagar, K. Kern, K. Balasubramanian, Nanotechnology 2010, 21, DOI 10.1088/0957-4484/21/1/015303.
[27] J. Kim, F. Kim, J. Huang, Mat. Today 2010, 13, 28-38.
[28] L. Xie, X. Ling, Y. Fang, J. Zhang, Z. Liu, J. Am. Chem. Soc. 2009, 131, 9890-+.
[29] I. Calizo, W. Bao, F. Miao, C. Lau, A. Balandin, Appl. Phys. Lett. 2007, 91, DOI 10.1063/1.2805024.
[30] H. Cao, Q. Yu, R. Colby, D. Pandey, C. Park, J. Lian, D. Zemlyanov, I. Childres, V. Drachev, E. Stach, M. Hussain, H. Li, S. Pei, Y. Chen, J. Appl. Phys. 2010, 107, DOI 10.1063/1.3309018.
[31] Y. Wang, Z. Ni, T. Yu, Z. Shen, H. Wang, Y. Wu, W. Chen, A. Wee, J. Phys. Chem. C 2008, 112, 10637-10640.
[32] A. Reina, H. Son, L. Jiao, B. Fan, M. Dresselhaus, Z. Liu, J. Kong, J. Phys. Chem. C 2008, 112, 17741-17744.
[33] X. Li, Y. Zhu, W. Cai, M. Borysiak, B. Han, D. Chen, R. D. Piner, L. Colombo, R. S. Ruoff, Nano Lett. 2009, 9, 4359-4363.

The invention claimed is:

1. A method for analyzing graphene comprising
performing fluorescence quenching microscopy on a graphene sample to identify graphene layers on arbitrary substrates, the fluorescence quenching microscopy includes:
applying a polymer mixed with fluorescent dye onto the graphene then viewing the sample under a fluorescence microscope, wherein the polymer and dye mixture is applied by spin-coating a solution of the polymer and dye mixture onto the graphene sample, wherein the solution include toluene; and wherein the graphene layers are identified by performing a histogram-based segmentation based on contrast relative to the substrates.

2. The method of claim 1 in which the polymer is a cured poly(methyl methacrylate).

3. The method of claim 2 in which the polymer is removed by soaking in acetone and including the initial step, prior to said soaking with acetone, of applying a small amount of either acetone or poly(methyl methacrylate) to the polymer and drying said applied acetone or poly(methyl methacrylate).

4. The method of claim 3 in which individual images of the graphene sample are obtained to collect a montage of the images.

5. The method of claim 3, in which the graphene layers are identified by performing a histogram-based segmentation based on contrast relative to the substrates.

6. The method of claim 5, wherein the segmentation step comprises of collecting a large-scale, high-resolution montage image of the sample and processing the image to remove the effects of non-uniform illumination.

7. The method of claim 6 wherein the effects of non-uniform illumination is removed by applying the polymer and dye mixture onto a substrate bare of graphene and creating a correction image thereof using the same imaging pathway used to create the montage image.

8. The method of claim 1 in which individual images of the graphene sample are obtained to collect a montage of the images.

9. The method of claim 8, in which the graphene layers are identified by performing a histogram-based segmentation based on contrast relative to the substrates.

10. The method of claim 9, wherein the segmentation step comprises of collecting a large-scale, high-resolution montage image of the sample and processing the image to remove the effects of non-uniform illumination.

11. The method of claim 10 wherein the effects of non-uniform illumination is removed by applying the polymer and dye mixture onto a substrate bare of graphene and creating a correction image thereof using the same imaging pathway used to create the montage image.

12. The method of claim 1, wherein the segmentation step comprises of collecting a large-scale, high-resolution montage image of the sample and processing the image to remove the effects of non-uniform illumination.

13. The method of claim 12 wherein the effects of non-uniform illumination is removed by applying the polymer and dye mixture onto a substrate bare of graphene and creating a correction image thereof using the same imaging pathway used to create the montage image.

14. A method for analyzing graphene comprising
performing fluorescence quenching microscopy on a graphene sample to identify graphene layers on arbitrary substrates, the fluorescence quenching microscopy including applying a polymer mixed with fluorescent dye onto the graphene then viewing the sample under a fluorescence microscope, wherein the polymer is removed by soaking in acetone and including the initial step, prior to said soaking with acetone, of applying a small amount of either acetone or poly(methyl methacrylate) to the polymer and drying said applied acetone or poly(methyl methacrylate).

15. A method for analyzing graphene comprising
performing fluorescence quenching microscopy on a graphene sample to identify graphene layers on arbitrary substrates, the fluorescence quenching microscopy including applying a polymer mixed with fluorescent dye onto the graphene then viewing the sample under a fluorescence microscope, and the graphene layers are identified by performing a histogram-based segmentation based on contrast relative to the substrates.

* * * * *